United States Patent [19]

Blaschke et al.

[11] Patent Number: 4,973,745

[45] Date of Patent: Nov. 27, 1990

[54] PROCESS FOR OBTAINING ENANTIOMERS OF 2-ARYLPROPIONIC ACIDS

[75] Inventors: Gottfried Blaschke; Karl-Ernst Schulte, both of Münster, Fed. Rep. of Germany

[73] Assignee: Medice Chem.-Pharm. Fabrik Pütter GmbH & Co. KG, Iserlohn/Westfalen, Fed. Rep. of Germany

[21] Appl. No.: 345,716

[22] Filed: May 1, 1989

[30] Foreign Application Priority Data

May 2, 1988 [DE] Fed. Rep. of Germany ....... 3814887

[51] Int. Cl.$^5$ ............................................. C07B 55/00
[52] U.S. Cl. ..................................... 562/401; 548/224
[58] Field of Search ......................... 562/401; 548/224

[56] References Cited

U.S. PATENT DOCUMENTS 4,209,638 6/1980 Nicholson et al. .................. 562/401
4,621,152 11/1986 Bernini ................................ 562/401
4,675,054 11/1986 Bernini ................................ 562/401

FOREIGN PATENT DOCUMENTS 408943 10/1973 U.S.S.R. ............................. 562/401

OTHER PUBLICATIONS

S. S. Adams, et al., "Pharmacological Difference Between the Optical Isomers of Ibuprofen: Evidence for Metabolic Inversion of the (−)-Isomer." J. Pharm, Pharmac., 28: 156–157, 1976.

F. Hanakum et al., "Pharmacokinetics of Ibuprofen Enantiomers in Humans Following Oral Administration of Tablets with Different Absoprtion Rates." Pharm. Res., 5(1): 40–43, 1988.

*Primary Examiner*—Bruce Gray
*Attorney, Agent, or Firm*—Scully, Scott, Murphy & Presser

[57] ABSTRACT

A process for obtaining enantiomers of 2-arylpropionic acids by reacting a racemic mixture thereof with an amine-enantiomer, which process comprises converting the racemate of the 2-arylpropionic acid with an optically active form of threo-1-p-nitrophenyl-2-aminopropane-1,3-diol into the diastereomeric salts, separating these salts and converting the thus-obtained pure diastereomers into the free acids of the enantiomer forms of the 2-arylpropionic acid or into the salts thereof.

5 Claims, No Drawings

PROCESS FOR OBTAINING ENANTIOMERS OF 2-ARYLPROPIONIC ACIDS

This application pertains to a process for obtaining enantiomers of 2-arylpropionic acids by reacting a racemic mixture thereof with an amine-enantiomer.

Many 2-arylpropionic acids are applied in the form of their racemic mixtures for rheuma therapy due to their analgesic and antiphlogistic properties. The mechanism of action could occur via the inhibition of the "arachidon acid cascase" (formation of prostaglandines, thromboxanes, leukotrienes).

Generally, the mixtures used contain both antipodes of the 2-arylpropionic acids which, however, are not equal as to their pharmacological activity. Nevertheless, for therapy the uncleaved mixtures are normally still being used, with the exception of naproxene being used in the S-form. Therefore, there is a need for simple methods of obtaining the pure antipodes. Thus, Adams et al. (J. Pharm. Pharmakol. 28, 256-257) found that e.g. the S(+)-ibuprofen inhibits in vitro the prostaglandin-synthetase 160 times stronger than the R(−)-isomer. Meanwhile it was experimentally proven with animals and human patients that the S(+)-ibuprofen is the more potent pharmaceutical composition. With S(+)-ibuprofen the same therapeutic action can be achieved while administering a substantially lower dose compared with the racemate. Simultaneously, the side effects observed when applying the racemate in therapeutic doses do not occur or occur to a substantially lower extent.

The latter are apparently caused by the non or only slightly analgesically or antiphlogistically active R(−)-ibuprofen. The different pharmacological properties of the two antipodes of ibuprofen are also expressed by their different pharmacokinetics and biotransformation (F. Jamali et al., Pharmac. Res. 5, 44 (1988)).

The manufacture of the optically pure 2-arylpropionic acids on a technical scale can be carried out by a stereospecific synthesis of the pharmaceutical composition or by splitting the racemate. For the stereospecific synthesis a Friedel-Craft-Synthesis for ibuprofen could be considered, e.g. reacting isobutylbenzene with optically active lactic acid derivatives (e.g. S(+)-mesyl-lactic acid methylester) or R(−)-chloropropionic acid isobutylester. Generally the syntheses occur due to isomerisations but with bad yields.

The separation of a racemic mixture of 2-arylpropionic acids is described in US-A-4209638 (Boots Company Ltd., Nottingham). It is carried out by a fractionated crystallization of the diastereomeric salts formed by the two acids with an optically active base. As a base the L-form of α-methyl or aryl-substituted benzylamines are used, with which the S(+)- and R(−)-forms of the 2-arylpropionic acids generate diastereomeric salts having different solubility in aliphatic hydrocarbons, and mixtures of these hydrocarbons and aromates respectively. Thereby, the diastereomeric salts can be separated from each other. The acids can be obtained from the pure diastereomeric salts by conventional methods with dilute mineral acids.

For various reasons this process is not being used. Due to the several recrystallization operations which are necessary, this process not only requires time but is also uneconomical, as it only leads for example to low yields. Moreover, the bases used are expensive and chemically unstable; they are only regainable in a pure state with losses. Other optically active bases, such as ephedrin, pseudoephedrin, norephedrin or norpseudoephedrin, yield with typical 2-arylpropionic acids, e.g. with S(+)- and R(−)-ibuprofen respectively, no crystalline diastereomeric salts.

Surprisingly, it has now been found that for separating the racemate of 2-arylpropionic acids the amino alcohol threo-1-p-nitrophenyl-2-aminopropane-1,3-diol is specially suited. This amino alcohol, which readily crystallizes, which is stable against oxygen and acids and which does not racemize under normal conditions, forms with S(+)- and R(−)-antipodes diastereomeric salts being readily separated from simple organic solvents and solvent mixtures.

The object of this invention is to provide a process according to claim 1 of this application, which process comprises converting the racemate of the 2-arylpropionic acid with an optically active form of threo-1-p-nitrophenyl-2-aminopropane-1,3-diol, preferably the D(−)-form, into the diastereomeric salts, separating these salts and converting the thus-obtained pure diastereomers into the free acids of the enantiomer forms of the 2-arylpropionic acid or the salts therefrom.

As 2-arylpropionic acids used in the process according to the invention, especially flurbiprofen, fenoprofen, ketoprofen, naproxen, benoxaprofen and ibuprofen should be named.

The use of the amino alcohol mentioned above leads to the formation of diastereomeric salts which dissolve very differently in organic solvents. In this way it is possible to cleave the optical antipodes, e.g. by crystallization. A suitable solvent can be found out by simple tests carried out by a person skilled in the art. Normally, unpolar solvents are applied to which a portion of polar solvents can be added. Such unpolar solvents can be aliphatic, alicyclic and aromatic hydrocarbons, e.g. petroletherfractions (boiling point: 60-90° C.), cyclohexane etc., the polar component being preferably e.g. a lower preferably aliphatic alcohol. Such alcohols could be methanol, ethanol, i-propanol, etc. Thus, suitable solvent mixtures are e.g. cyclo-hexane-ethanol, petrolether-isopropanol, etc.

The invention will now be explained in more detail illustrating the separation of the racemic mixture of ibuprofen, the therapeutically more important S(+)-antipode being obtainable in a simple manner in high purity. The statements concerning this matter can be applied analogously to the other representatives of the therapeutically used 2-arylpropionic acids, the invention being therefore not restricted to these preferred features of the process according to the invention:

The diastereomeric salt from S(+)-ibuprofen and said amino alcohol precipitates at room temperature with good yields from a mixture of isopropanol and petrolether 1:10, whilst the salt of the R(−)-form with the amino alcohol remains extensively in solution.

The diastereomeric salt can be obtained by recrystallization, e.g. from a mixture of isopropanol and petrolether of 1:1 to 5 in such a pure form that the S(+)-form of ibuprofen freed after acidification with mineral acid yields with an optical purity of 95 to 99%.

From the crystalline salt the amino alcohol can be separated in crystalline form by the action of a weak base saturated at RT, preferably $Na_2CO_3$ solution (pH 11). From the solution thus obtained, S(+)-ibuprofen can be gained in crystalline form by adding mineral acid, e.g. 10N hydrochloric acid.

It was found that the process according to the invention can be operated economically by regaining the amino alcohol in practically a chemically and optically pure form, the R(−)- and S(+)-acids remaining in the mother liquors being reusable by racemization. By precipitating the diastereomeric salt as well as recrystallizing this salt mother liquors are generated which contain the R(−)- and S(+)-2-arylproprionic acid and the base. After carefully removing the solvent (petrolether, isopropanol) the remainder can be converted into a hydrous solution e.g. with hydrous alkali, preferably potassium hydroxide. Thereby, a further portion of the amino alcohol separates in crystallized form. From the separated solution the two enantiomer acids are obtained after acidification. In this acid mixture, in which with ibuprofen the proportion of the R(−)-form predominates, the two acids can be racemized with or without the addition of small amounts of a catalyst in the presence or absence of a solvent (namely water) at temperatures of 100 to 250° C. at normal or elevated pressure respectively. Thereby, a mixture of the two acids is obtained, which as to its composition corresponds to the starting material of the racemic product, e.g. with ibuprofen. This racemate can be introduced again into the crystallization process for separating the S-form after addition of the optically active amino alcohol.

The process can be carried out economically by regaining the base and racemizing the remaining component, e.g. the R(−)-ibuprofen. The base is regainable to more than 80% ($[\alpha]_D^{20}$: −28.0° to −30.5°). The yields are high, e.g. for S(+)-ibuprofen with 95-99% optical purity ($[\alpha]_D^{20}$:=57.6°) 95-100% of the starting racemic ibuprofen. The invention is illustrated in the following typical, but also preferred examples:

EXAMPLE 1

1-3 moles (206.3 to 618.9 g) racemic ibuprofen are suspended with 1 mol (212.2 g) D(−)-threo-1-p-nitrophenyl-2-aminopropane-1,3-diol in 420 to 850 ml isopropanol, the suspension being heated to a clear solution. To this solution are added while heating 2.2 to 8.5 l petrolether (bp. 60-90° C.), the solution being heated until a clear solution has formed. The solution is cooled down with or without stirring to circa 20-25° C. (RT). Crystallization occurs. The crystals are separated rapidly from the mother liquor (yield circa 58-65% related to a diastereomeric salt (1:1) from S(+)-ibuprofen and the amino alcohol).

The crystalline salt is recrystallized from a mixture of isopropanol and petroether 1:4: yield 80-85%. Then the salt is suspended in a hydrous saturated sodium carbonate solution. The amino alcohol precipitates in crystalline form: yield 35-50%, related to the starting amount of amino alcohol. The acid being dissolved as sodium salt is precipitated by acidifying with a mineral acid in crystalline form with an optical purity of 95-99% and a yield of 80-85% related to the first crystallizate.

The mother liquors produced by the first precipitation of the diastereomeric salt and by the recrystallization of this salt are combined and freed from the solvent mixture (e.g. by vacuum distillation or steam distillation). The obtained oily remainder is treated with hydrous potassium hydroxide. The amino alcohol crystallizes (yield: 22-30% of the starting amount). The dissolved acids of S(+)- and R(−)-ibuprofen can be separated in crystalline form by acidifying with mineral acid. The dried acids are heated for a short time to temperatures between 100 and 250° C. with or without a small amount of catalyst, e.g. potassium hydroxide or sodium ibuprofenate, with or without solvent (e.g. water) at normal or elevated pressure. A racemization occurs yielding a mixture of S(+)- and R(−)-ibuprofen, which as to its composition corresponds to the starting substance of the racemic ibuprofen introduced into the process.

This racemate again can be introduced into the separation process after addition of the optically active amino alcohol, which also can be obtained from the mother liquors.

Total yield:

S(+)-ibuprofen with an optical purity of 95-99% ($[\alpha]_D^{20}$: +57.6) in a yield of 95-98% of the starting racemate.

Amino alcohol circa 80% ($[\alpha]_D^{20}$: −28.0 to −30.5; Fp. 162-167, (decomposition) of the starting amount.

EXAMPLE 2

1.0 mol (230.2 g) racemic naproxen and 0,5 mol (106.1 g) L-(+)-threo-1-p-nitrophenyl-2-aminopropane-1,3-diol are dissolved in 3.5 l isopropanol while heating. Then the solution is kept at 5° C. for 24 hours. Crystallization occurs: yield 152 g (=68.72% of a 1:1 salt from amino alcohol and S(+)-naproxen). Fp.: 167-169° C.; optical purity of the acid contained in the salt: 15.2%.

After recrystallizing the precipitated salt two times from isopropanol, the salt is obtained in a yield of 54.2 g (=24.5% related to a 1:1 salt from amino alcohol and S(+)-naproxen). The acid contained in the salt has an optical purity of 90%.

50 g of the diastereomeric salt are suspended in 500 ml water, 50 ml 2 N sulfuric acid are added and stirred at room temperature for ½ hr.: the acid set free precipitates, yield 28.1 g (=99.5%); Fp. 152-155° C. The acid corresponds to 24.38% of the S(+)-naproxen of the racemic naproxen; the optical purity of the acid is 90.6%.

The recovery of the base is carried out as described in Example 1 with a yield of 80-85%; Fp. 163-166° C. $[\alpha]_D^{20}$:28-30°. The mixture of R(−)-naproxen and S(+)-naproxen set free from the mother liquors is racemized and again recycled to the separating operation.

Total yield: S(+)-naproxen 87-93% in 90-95% optical purity (related to the starting racemic naproxen); Fp. 154-155° C. $[\alpha]_D^{20}$=+65.2.

L-(+)-threo-1-p-nitrophenyl-2-aminopropane-1,3-diol: 75-82% yield, Fp.=163-166° C. $[\alpha]_D^{20}$=+28.0-29.3°.

EXAMPLE 3

1.0 mol (244.3 g) racemic flurbiprofen and 0.5 mol (106.1 g) D-(−)-threo-1-p-nitrophenyl-2-aminopropane-1,3-diol are dissolved in 350 ml isopropanol while heating. Then 2 l petroether (60-90°), which is heated to the temperature of the isopropanol solution, are added. The mixture is kept at room temperature for 20 hrs. Crystallization occurs: yield 195.0 g (=67.65% of a salt from the amino alcohol, S(+)-flurbiprofen and isopropanol (1:1:1); Fp. 127-128°. The optical purity of the acid contained in the diastereomeric salt is 10.2%. After recrystallizing the salt from isopropanol two times: yield 150.0 g (=52.04% of a salt from amino alcohol, S(+)-flurbiprofen and isopropanol (1:1:1); Fp. 130-132° C., optical purity of the acid contained in the salt 24.2%. Renewed crystallization of the salt from ethyl acetate: yield 110 g (=48.20% related to a 1:1 salt from amino alcohol and S(+)-flurbiprofen). The optical purity of the S(+)-flurbiprofen is 35%. A repeated recrystallization yields an acid with the optical purity of 90-95%.

According to known methods, the diastereomeric salt is split by the addition of 2N sulfuric acid, the liberation of the acid occurs with quantitative yields.

The recovery of the base from the diastereomeric salt and the mother liquors respectively is carried out according to Example 1. From the same substrate the acid mixture (R(−)-flurbiprofen and S(+)-flurbiprofen) is isolated and then racemized according to known methods.

Total yield: S(+)-flurbiprofen: 85-90% of the starting racemate; Fp. 100-103° C.; optical purity: 90-95% $[\alpha]_D^{20}=43.85$.

D-(−)-threo-1-p-nitrophenyl-2-aminopropane-1,3-diol: 80-85%, Fp.=162-166° C. $[\alpha]_D^{20}=+28-30°$.

EXAMPLE 4

1.0 mol (273.7 g) racemic carprofen and 0.5 mol (106.1 g) D-(−)-threo-1-p-nitrophenyl-2-aminopropane-1,3-diol are dissolved in 390 ml acetone while heating. Then the solution is kept at circa 5° C. for 5 hrs. Crystallization occurs: yield 140 g (=57.63% related to a salt (1:1) from amino alcohol and S(+)-carprofen); Fp. 204-205° C.; the acid contained in the salt has an optical purity of 52%.

104 g of the obtained crystalline compound are recrystallized from 220 ml acetone (at 5° C. for 2 hrs.). Yield: 46.7 g (=19.22% related to a salt (1:1) from amino alcohol and S(+)-carprofen). Fp. 209-210° C. The acid contained in the salt has an optical purity of 81.2%; renewed recrystallization: 92-95%.

The mother liquor generated is concentrated to half of its volume and cooled to 5° for 24 hrs. The precipitating crystallizate is separated and dried: yield: 47.8 g (=19.67% related to a salt (1:1) from the amino alcohol and S(+)-carprofen); Fp. 208-209° C. The acid contained in the salt has an optical purity of 61.8%. Renewed recrystallization: 92-95%. 50 g of the diastereomeric salt are suspended in 500 ml of water at room temperature, the suspension is reacted with 50 ml 2N sulfuric acid and stirred at room temperature for 30 min. White crystals precipitate which are dried. Yield: 28.0 g (=99.5% related to the acid S-component of the salt); Fp. 202-205° C. The optical purity of the acid set free is 91.5% (related to S(+)-carprofen).

The base is regained from the diastereomeric salt and the mother liquors as described in Example 1 and the mixture from R(−)-carprofen and the remainder of S(+)-carprofen set free is racemized. The base as well as the racemic carprofen are again introduced into the separating operation.

Total yield:

S(+)-carprofen with an optical purity of 92-95% $[\alpha]_D^{20}=52.8°$, circa 95% of the starting racemate; Fp. 202-205° C. Amino alcohol: yield: circa 85% $[\alpha]_D^{20}=-28.0$ to $-30.5$.

What is claimed is:

1. A process for obtaining S-enantiometers of 2-arylpropionic acids by reacting a racemic mixture thereof with an optically active form of threo-1-nitrophenyl-2-aminopropane-1,3-diol which process comprises converting the racemate of a 2-arylpropionic acid selected from the group consisting essentially of flurbiprofen, carprofen and ibuprofen with D-(−)-threo-1-nitro-phenyl-2-aminopropane-1,3-diol into the diastereomeric salts of said 2-arylpropionic acids, separating said salts and isolating the S-enantiomer forms of the said -2arylpropionic acid or the salts thereof from the resulting pure diastereomers.

2. A process according to claim 1, wherein the diastereomeric salts are split by crystallization.

3. A process according to claim 1, comprising concentrating the mother liquor remaining after precipitating the salt of the optical antipode, by adding moter liquor from the recrystallization of the separated antipode, forming a slurry with hydrous alkali and separating therefrom the amino alcohol.

4. A process according to claim 1 comprising racemizing again the solution of the enantiomers of 2-arylpropionic acid obtained after separating the precipitated salt of the optical antipode and of the amino alcohol and recycling the solution into the process.

5. A process according to claim 1 in which ibuprofen is used as racemic mixture and S(+)-ibuprofen is obtained therefrom.

* * * * *

UNITED STATES PATENT AND TRADEMARK OFFICE
CERTIFICATE OF CORRECTION

PATENT NO. : 4,973,745

DATED : November 27, 1990

INVENTOR(S) : Gottfried Blaschke, et al.

It is certified that error appears in the above-identified patent and that said Letters Patent is hereby corrected as shown below:

Column 6, line 32, Claim 3: "moter" should read as --mother--

Signed and Sealed this

Nineteenth Day of May, 1992

Attest:

DOUGLAS B. COMER

Attesting Officer

Acting Commissioner of Patents and Trademarks